United States Patent [19]

Fanshawe et al.

[11] 4,118,393

[45] Oct. 3, 1978

[54] PHENYL AZABICYCLOHEXANONES

[75] Inventors: William Joseph Fanshawe, Pearl River, N.Y.; Sidney Robert Safir, River Edge, N.J.; Lantz Stephen Crawley, Spring Valley, N.Y.

[73] Assignee: American Cyanamid Company, Stamford, Conn.

[21] Appl. No.: 809,341

[22] Filed: Jun. 23, 1977

[51] Int. Cl.$^2$ .................. C07D 209/52; C07D 471/08
[52] U.S. Cl. ............................... 260/326.5 B; 424/274
[58] Field of Search .................................. 260/326.5 B

[56] References Cited

U.S. PATENT DOCUMENTS

| | | | |
|---|---|---|---|
| 3,166,571 | 1/1965 | Izzo et al. | 260/326.5 B |
| 3,932,429 | 1/1976 | Takeda et al. | 260/326.5 B |
| 3,972,994 | 8/1976 | Beregi et al. | 260/326.5 B |

*Primary Examiner*—Jose Tovar
*Attorney, Agent, or Firm*—Claude J. Caroli

[57] ABSTRACT

Substituted phenyl azabicyclohexanones, their method of preparation, and their conversion into substituted phenyl azabicyclohexanes which are active anxiolytic and analgesic agents.

12 Claims, No Drawings

PHENYL AZABICYCLOHEXANONES

BACKGROUND OF THE INVENTION

Applicants are not aware of any prior art references which, in their respective judgment as one skilled in the art, would anticipate or render obvious the novel compounds of the instant invention; however, for the purpose of fully developing the background of the invention and establishing the state of the requisite art, the following reference is set forth: U.S. Pat. No. 3,166,571.

SUMMARY OF THE INVENTION

This invention is concerned with optically active lactams of the formulae:

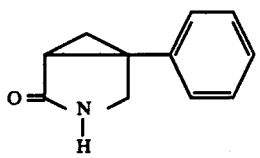 (I)

and

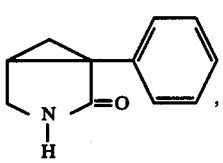 (II)

wherein the phenyl moiety is unsubstituted, mono-substituted or di-substituted from the group consisting of halogen, straight chain $C_1$–$C_6$ alkyl, $C_1$–$C_6$ alkoxy, nitro, amino, trifluoromethyl, acetamindo and hydroxy; the racemic mixture thereof; and the mirror image thereof.

A preferred embodiment of the instant invention consists of those compounds wherein the phenyl moiety is di-substituted from the group consisting of halogen, straight chain $C_1$–$C_6$ alkyl, $C_1$–$C_6$ alkoxy, trifluoromethyl, nitro, amino, acetamido and hydroxy.

A second preferred embodiment of the instant invention consists of those compounds wherein the phenyl moiety is unsubstituted or mono-substituted from the group consisting of halogen, straight chain $C_1$–$C_6$ alkyl, $C_1$–$C_6$ alkoxy, trifluoromethyl, nitro, amino, acetamido and hydroxy.

A most preferred embodiment of the second preferred embodiment consists of those compounds wherein the phenyl moiety is para or meta substituted from the group consisting of straight chain $C_1$–$C_6$ alkyl, halogen and trifluoromethyl.

A still further preferred embodiment of the most preferred embodiment consists of those compounds wherein the phenyl moiety is para or meta substituted from the group consisting of methyl, ethyl, chloro, fluoro, bromo and trifluoromethyl.

DESCRIPTION OF THE INVENTION

The novel optically active lactams of formula (I) may be prepared from a suitably phenyl substituted cyano ester of the formula:

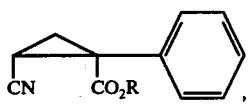

wherein R is selected from the group consisting of $C_1$–$C_6$ alkyl, which comprises reducing said cyano ester with diborane in a solvent such as tetrahydrofuran, at a temperature from about 0° to about 60° C., from about 1 to about 3 hours; and reacting the intermediate reduction product with a mineral acid such as 6N hydrochloric acid. The novel optically active lactams of formula (II) may be prepared from a suitably phenyl substituted cyano ester of the formula:

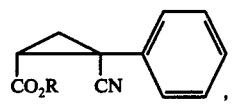

wherein R is selected from the group consisting of $C_1$–$C_6$ alkyl; which comprises following the procedure shown immediately above.

The compounds of this invention are useful as intermediates for the preparation of the following compounds which are anxiolytic and analgesic agents:

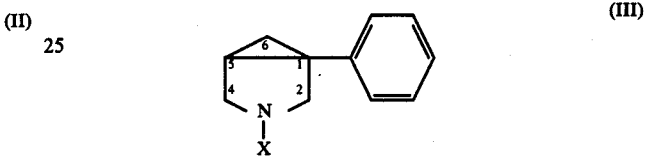 (III)

wherein the phenyl moiety is unsubstituted or mono- or di-substituted from the group consisting of halogen, straight chain $C_1$–$C_6$ alkyl, $C_1$–$C_6$ alkoxy, trifluoromethyl, nitro, amino, acetamido and hydroxy; X is selected from the group consisting of hydrogen, straight chain $C_1$–$C_8$ alkyl, and a moiety of the formula $C_nH_{2n}R_1$; wherein n is an integer from 1 to 3 and $R_1$ is selected from the group consisting of phenyl and p-fluorobenzoyl; the racemic mixture thereof; the mirror image thereof and the non-toxic pharmaceutically acceptable salts thereof.

A compound of formula (III) which is of particular interest is 1-(p-tolyl)-3-azabicyclo[3.1.0]hexane.

The novel optically active lactams of formulae (I) and (II) may be converted into the anxiolytic an analgesic compounds of formula (III) by the procedure set forth immediately below.

The azabicyclohexane compound of formula (III) are prepared by reacting the optically active lactams of formulae (I) or (II) with a suitable reducing agent such as lithium aluminum hydride, diborane, sodium bis(2-methoxyethoxy)aluminum hydride (70% solution in benzene), or the like, in an aprotic solvent such as ether, benzene, tetrahydrofuran, and the like, at a temperature from about 0° to about 80° C. for a period of from about one to about six hours. The solution is cooled and a strong base, such as potassium hydroxide, is added. The organic layer is concentrated and the azabicyclohexane compounds of formula (III) are collected by filtration.

DETAILED DESCRIPTION OF THE INVENTION

EXAMPLE 1

Ethyl 2-cyano-1-phenyl-cyclopropanecarboxylate

To a stirred suspension of 3.6 g of 57% sodium hydride in mineral oil in 150 ml of ether is added dropwise, under nitrogen, a solution of 9.7 g of ethyl-2-bromophenylacetate in 50 ml of ether, 4.2 g of acrylonitirle and 0.5 ml of ethanol dropwise at room temperature. The mixture is stirred overnight at room temperature. The excess hydride is decomposed by the cautious addition of 10 ml of ethanol and the mixture is diluted with 50 ml of water. The ether phase is separated and the aqueous phase is extracted with ether. The combined ethereal solutions are dried over magnesium sulfate and concentrated under reduced pressure to a black liquid. This liquid is distilled at 0.25 mm and the fraction boiling at 130°–132° C. is collected to yield the title compound.

EXAMPLE 2

1-Phenyl-3-azabicyclo[3.1.0]hexan-2-one

To a stirred solution of 0.60 g of the above ethyl ester in 10 ml of dry tetrahydrofuran is added 9 ml of 1M-diborane in tetrahydrofuran, dropwise during 10 minutes under nitrogen. The mixture is stirred at room temperature for 30 minutes and then the excess diborane is decomposed by slowly adding 5 ml of water. The mixture is diluted with 50 ml of water and extracted with ether. The ether extracts are dried over magnesium sulfate and concentrated under reduced pressure to an oil. Purification by silica gel chromatography gives the product as a yellow liquid.

EXAMPLE 3

1-p-Chlorophenyl-3-azabicyclo[3.1.0]hexan-2-one

To a stirred solution of 3.0 ml of sodium bis(2-methoxyethoxy)aluminum hydride is added dropwise a solution of 2.2 g of 1-(p-chlorophenyl)-1,2-cyclopropanedicarboximide (U.S. Pat. No. 3,344,026) in 200 ml of benzene, over a 45 minute period, at room temperature, under nitrogen. The mixture is refluxed under nitrogen for one hour. After cooling, 4 ml of 5N sodium hydroxide is added to decompose any excess hydride and the mixture is diluted with 200 ml of water. The benzene phase is separated. The aqueous phase is extracted with ether. The ether and benzene phases are combined, dried over magnesium sulfate and concentrated under reduced pressure to give a white glass which is recrystallized from benzene-hexane to give the product as a white solid, mp 132°–137 ° C. (dec).

EXAMPLE 4

Ethyl 1-cyano-2-phenyl-cyclopropanecarboxylate

The compound is prepared with ethyl acrylate and α-bromophenylacetonitrile using the procedure described in Example 1.

Example 5

1-Phenyl-3-azabicyclo[3.1.0]hexan-4-one

Treatment of ethyl-1-cyano-2-phenyl-cyclopropanecarboxylate using the procedure described in Example 2 gives the title product.

EXAMPLE 6

Preparation of 1-(p-Tolyl)-3-azabicyclo[3.1.0]-hexan-2-one

To a slurry of 5.0 g of sodium hydride (50% mineral oil dispersion) in 350 ml of ether, and 0.5 ml of methanol, is added a solution of 24.0 g methyl-bromo-p-tolylacetate, 8.0 g of acrylonitrile and 1.0 ml of methanol at 20°–28° C. over a one-half hour period. After stirring for an additional hour, 10 ml of methanol is added and the ether solution is washed with water. The organic phase is dried over sodium sulfate and the filtered solution is evaporated to give 5.5 g of yellow crystals. Recrystallization from ethanol gives 3.50 g of cis-2-cyano-1-methoxycarbonyl-1-(p-tolyl)cyclopropane as colorless cystals, mp 88°–91° C.

To a solution of 2.15 g of the cyano ester in 100 ml of dry tetrahydrofuran at 0° C. is added 7.5 ml of 1M borane-tetrahydrofuran. This solution is refluxed for 30 minutes and then is held at room temperature for 2 hours. To the cooled solution is added 10 ml of 6N hydrochloric acid, and this solution is warmed in a steam bath for 15 minutes and then is evaporated. The residue is extracted with dichloromethane and evaporation of the solution gives 1-(p-tolyl)-3-azabicyclo[3.1.0]-hexan-2-one as a colorless oil, i.r. 5.90 microns.

We claim:

1. An optically active compound of the formulae:

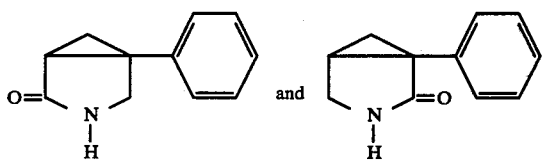

wherein the phenyl moiety is unsubstituted, mono- or di-substituted from the group consisting of halogen, straight chain $C_1$–$C_6$ alkyl, $C_1$–$C_6$ alkoxy, nitro, amino, trifluoromethyl, acetamido and hydroxy; and the racemic mixture thereof.

2. an optically active compound according to Claim 1, wherein the phenyl moiety is di-substituted from the group consisting of halogen, straight chain $C_1$–$C_6$ alkyl, $C_1$–$C_6$ alkoxy, trifluoromethyl, nitro, amino, acetamido and hydroxy.

3. An optically active compound according to Claim 1, wherein the phenyl moiety is unsubstituted or mono-substituted from the group consisting of halogen, straight chain $C_1$–$C_6$ alkyl, $C_1$–$C_6$ alkoxy, trifluoromethyl, nitro, amino, acetamido and hydroxy.

4. An optically active compound according to Claim 3, wherein the phenyl moiety is para or meta substituted from the group consisting of straight chain $C_1$–$C_6$ alkyl, halogen and trifluoromethyl.

5. An optically active compund according to Claim 4, wherein the phenyl moiety is para or meta substituted from the group consisting of methyl, ethyl, chloro, fluoro, bromo and trifluoromethyl.

6. The optically active compound according to Claim 1, 1-phenyl-3-azabicyclo[3.1.0]hexan-2-one.

7. The optically active compound according to claim 1, 1-p-chlorohpenyl-3-azabicyclo hexan-2-one.

8. The optically active compound according to claim 1, 1-phenyl-3-azabicyclo[3.1.0]hexan-4-one.

9. The optically active compound according to claim 1, 1-(p-tolyl)-3-azabicyclo[3.1.0]hexan-2-one.

10. The optically active compound according to claim 1, 1-(p-tolyl)-3-azabicyclo[3.1.0]hexan-4-one.

11. A method for the preparation of an optically active compound of the formulae:

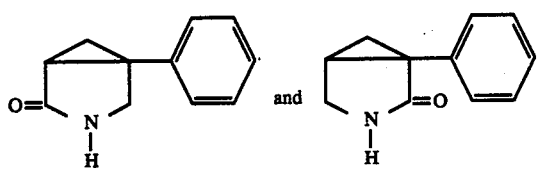
and wherein the phenyl moiety is unsubstituted, mono- or di-substituted from the group consisting of halogen, straight chain $C_1$–$C_6$ alkyl, $C_1$–$C_6$ alkoxy, nitro, amino, trifluoromethyl, acetamido and and the racemic mixture thereof; which comprises reducing a phenyl cyano ester of the formulae:

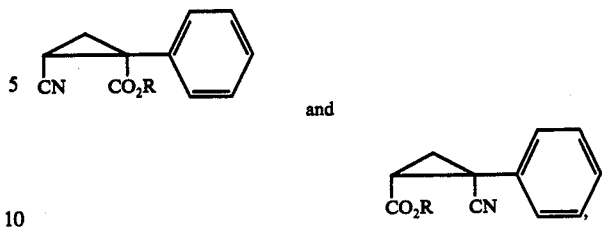
and wherein the phenyl moiety is unsubstituted, mono- or di-substituted as previously defined and R is selected from the group consisting of $C_1$–$C_6$ alkyl; with diborane, in a solvent, at a temperature from about 0° to about 60° C., from about one to about three hours; and reacting the intermediate reduction product with a mineral acid.

12. A method according to Claim 11, wherein said solvent is tetrahydrofuran, and said mineral acid is 6N hydrochloric acid.

* * * * *